United States Patent
Abdelkader

(10) Patent No.: US 11,801,110 B2
(45) Date of Patent: Oct. 31, 2023

(54) TRAY FOR BREAST VOLUME MEASUREMENT

(71) Applicant: Rasha Mohamed Abdelkader, Giza (EG)

(72) Inventor: Rasha Mohamed Abdelkader, Giza (EG)

( * ) Notice: Subject to any disclaimer, the term of this patent is extended or adjusted under 35 U.S.C. 154(b) by 451 days.

(21) Appl. No.: 16/827,670

(22) Filed: Mar. 23, 2020

(65) Prior Publication Data

US 2021/0290334 A1  Sep. 23, 2021

(51) Int. Cl.
*H02H 1/00* (2006.01)
*A61B 90/00* (2016.01)
*A61F 2/12* (2006.01)

(52) U.S. Cl.
CPC ............... *A61B 90/06* (2016.02); *A61F 2/12* (2013.01); *A61B 2090/063* (2016.02)

(58) Field of Classification Search
None
See application file for complete search history.

(56) References Cited

U.S. PATENT DOCUMENTS

| | | | |
|---|---|---|---|
| 4,024,856 A * | 5/1977 | Kirianoff | A61B 5/4312 623/7 |
| 4,219,029 A | 8/1980 | Grossman et al. | |
| 5,823,852 A | 10/1998 | Chu | |
| 6,796,875 B1 | 9/2004 | Placik | |
| 2019/0183408 A1 | 6/2019 | Tezcan | |

FOREIGN PATENT DOCUMENTS

CN   202015172 U   10/2011

* cited by examiner

*Primary Examiner* — Stephen W Jackson
(74) *Attorney, Agent, or Firm* — Sughrue Mion, PLLC

(57) ABSTRACT

This disclosure relates generally to a device for measuring the volume of a female breast. The disclosure is more particularly comprising of a cup-like template of variable size to embrace a breast to be measured and having an interior wall located in proximity to a breast to be measured and the cup-like template further comprises openings permit passage of excess fluid out of the space between said interior wall and the patient's breast as fluid is injected into said space, a sealing means all around periphery thereof for contact with a patient's skin of the breast to be measured, connector means in said template for passage of a fluid into the space formed between said interior wall and the breast to be measured when the template is sealed against the patient's skin by said sealing means, and a container for measuring the volume of fluid.

13 Claims, 5 Drawing Sheets

TRAY FOR BREAST VOLUME MEASUREMENT

TECHNICAL FIELD

Current disclosure is about a simple method that provides measurable, objective data that ensures breast symmetry in a large number of patients.

SUMMARY

Disclosed is an algorithmic measurement data tool, method and device used to standardize bra cup sizing, that can be useful to women, surgeons, and bra manufacturers to provide consistency and realistic expectations of breast sizes. The method utilizes measurement of the breast hemi circumference, used in conjunction with a standardized scale developed according to measurement results obtained, to accurately determine the woman's cup size. Tools, such as a slide rule, a Software program, and 3D imaging may also be used, establishing the breast hemi circumference, to determine the proper bra size. The tool documents and algorithmically compares documented hemi circumference measurements to actual reported cup sizes and manufacturers. This tool, method and publication The purpose of this disclosure is to provide a device for measuring the volume of a female breast that is simple to use, accurate and economical, that can be used by a breast surgeon with various types of operations performed on the breasts and that can be used by women for their personal breast size determinations conveniently. The device is characterized as being selectively adjustable to contain a breast in a suitably compressed configuration, which can be measured volumetrically by calibration indicia on the device.

Prior art methods measure the volume of the required implants during the surgery. For example, by inserting an elastic balloon into the patient's breast and measuring the amount of fluid injected into the balloon necessary to achieve the desired breast size. Once the physician determines that the desired breast size has been achieved, the fluid and balloon are removed and replaced by a prosthesis of volume corresponding to that of the fluid injected into the balloon. Prior art methods are, however, inexact, and do not permit accurate verification of the required implant size during surgery, such that the result may not conform to the patient's pre-operative prerequisites. Moreover, extant devices used to measure the volume of the prostheses do not provide an objective verification that the post-operative breast closely conforms to the pre-operative requirements.

Accordingly, it is desirable to provide an accurate device that can be used to reach the desired size of the breast and to measure the required volume of the breast prostheses during surgery, and to be a follow up tool to monitor any change in the breast size.

The present invention, wherein in one aspect device is provided that in some embodiments can be used to identify the desired size of the breast pre and post-operative, to measure the volume of the implant required to achieve the desired post-operative breast size, to verify that the post-operative breast size corresponds to the patient's desires and in another circumstances may be used as a follow up tool to monitor breast size.

DETAILED DESCRIPTION

The many features and advantages of the disclosure are apparent from the detailed specification, and thus, it is intended by the appended claims to cover all such features and advantages of the disclosure which fall within the true spirit and scope of the invention. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the invention.

Figure 1:
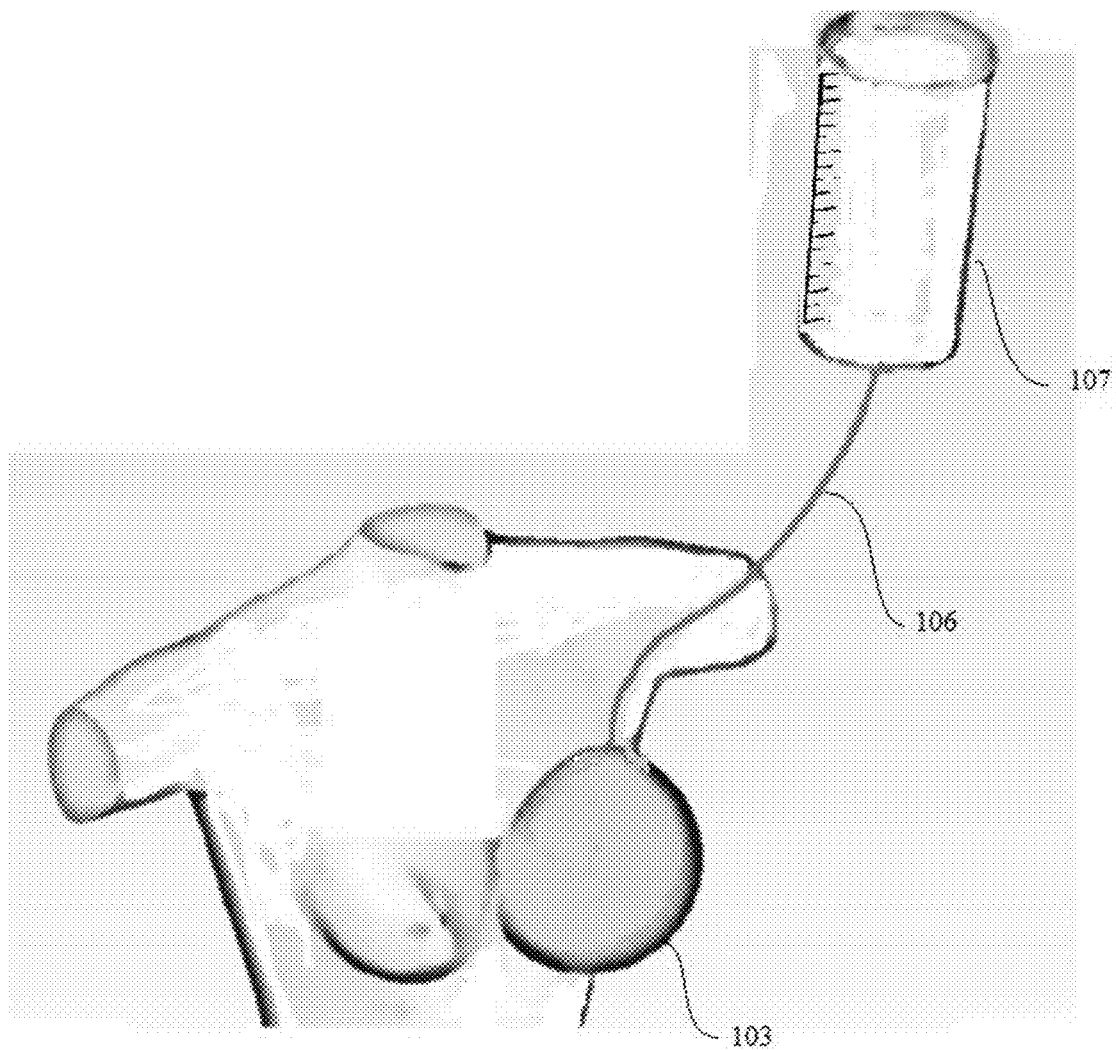
FIG. 1 illustrates breast volume measuring device as an embodiment of the current invention

FIG. 1, illustrates breast volume measuring device 101 wherein a female patient whose breast 102 is to be measured. A first embodiment of the disclosure is a cup shaped template 103, which may be located on the desired breast for measurement and, held in place by retaining means such as a fluid proof sealant 104 all around the periphery of the template and skin. The cup shaped template 103 as an embodiment of the current disclosure may be of variable size to fit many breast volumes based on a survey study about the mean breast volume among a chosen population.

Figure 2:
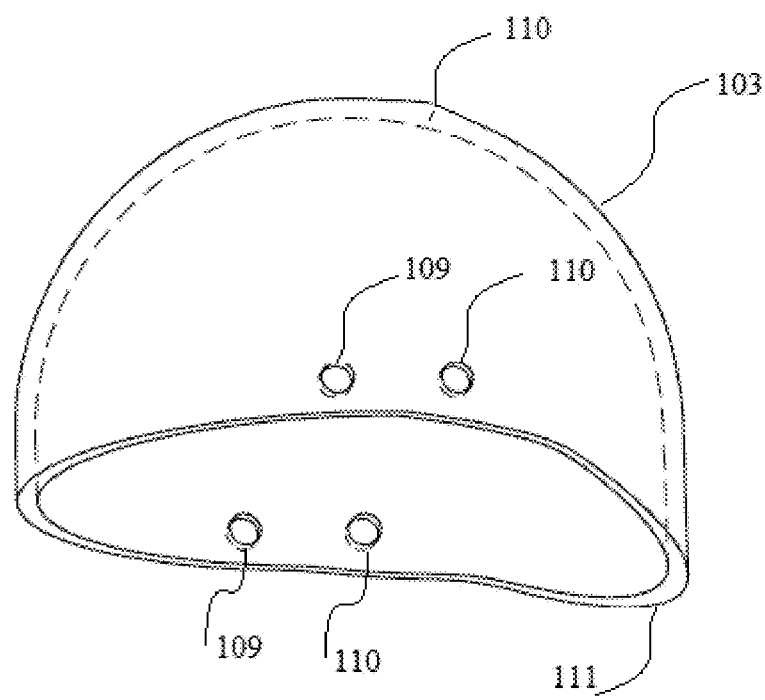
FIG. 2 illustrates the cup shaped template 103 as an embodiment of the current invention FIG. 3 a side view of the cup shaped template 103 as an embodiment of the current disclosure with showing detailed dimensions
Figure 3:
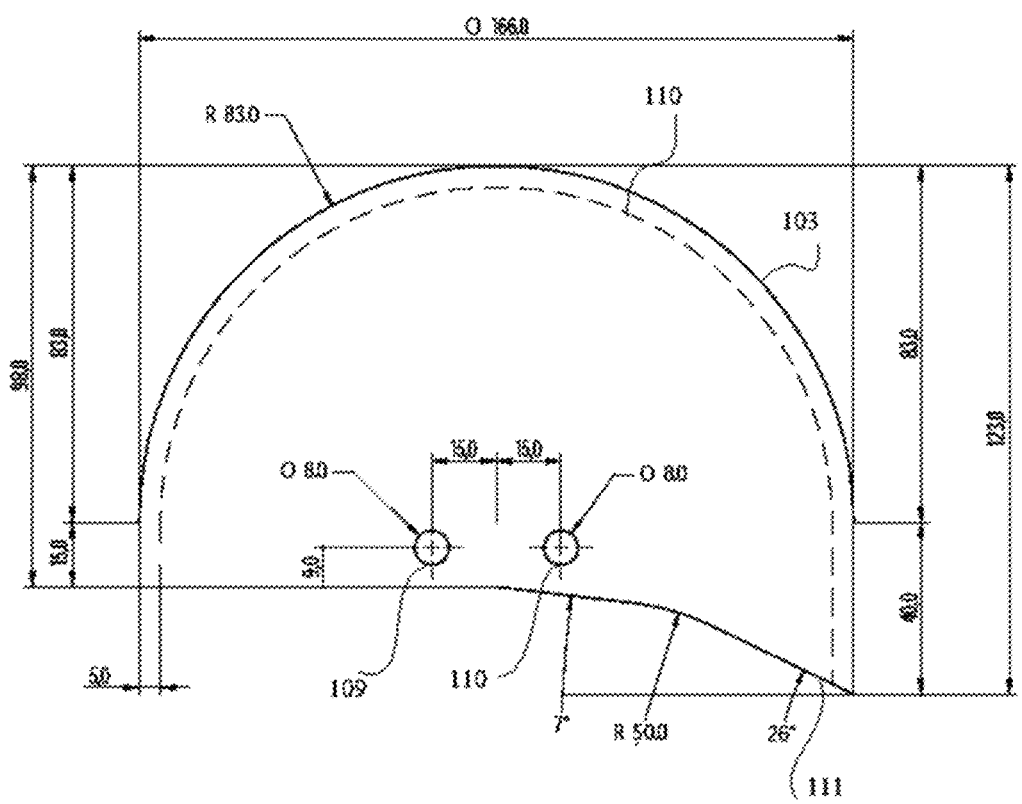

Referring to FIGS. 2-3, in another embodiment of the current disclosure each template has a cup portion appropriately designed to embrace the entire breast 102 having an interior wall located in proximity to the breast 102 to be measured and a space 105 is formed between the breasts 102 and the cup of the template 103. The periphery of the cup as shown in the figure has at its lower extended 113 part to ensure appropriate fit to the patient's chest wall 114 thus preventing leakage of the fluid while measuring breast volume.

FIG. 3 Illustrates a side view of the cup portion. The figure illustrates the cup's dimensions. The cup portion front part is a substantially hemispherical shaped having a diameter of approximately 166 O to and radius of approximately 83 O. It further includes four openings, two at each side of the cup portion. The openings are situated 9 O from the periphery of the cup portion and are 15 O from midline of the cup portion and lie 30 O from each other. Said openings, one opening to be attached to a tube attached to a fluid container and the other is to expelled air. The cup lower edge as shown in the figure bends with an angle approximately 7° to 26°. This renders the lower part 113 of the cup portion extends on the chest wall 114 beneath the breast 102 of the patient to ensure appropriate fit on the patient's chest wall 114. The cup portion is 98 O from above and 123 O from below creating a 40 O extended part on the chest wall of the patient as explained before. The cup portion thickness is approximately 5 O.

Figure 4:
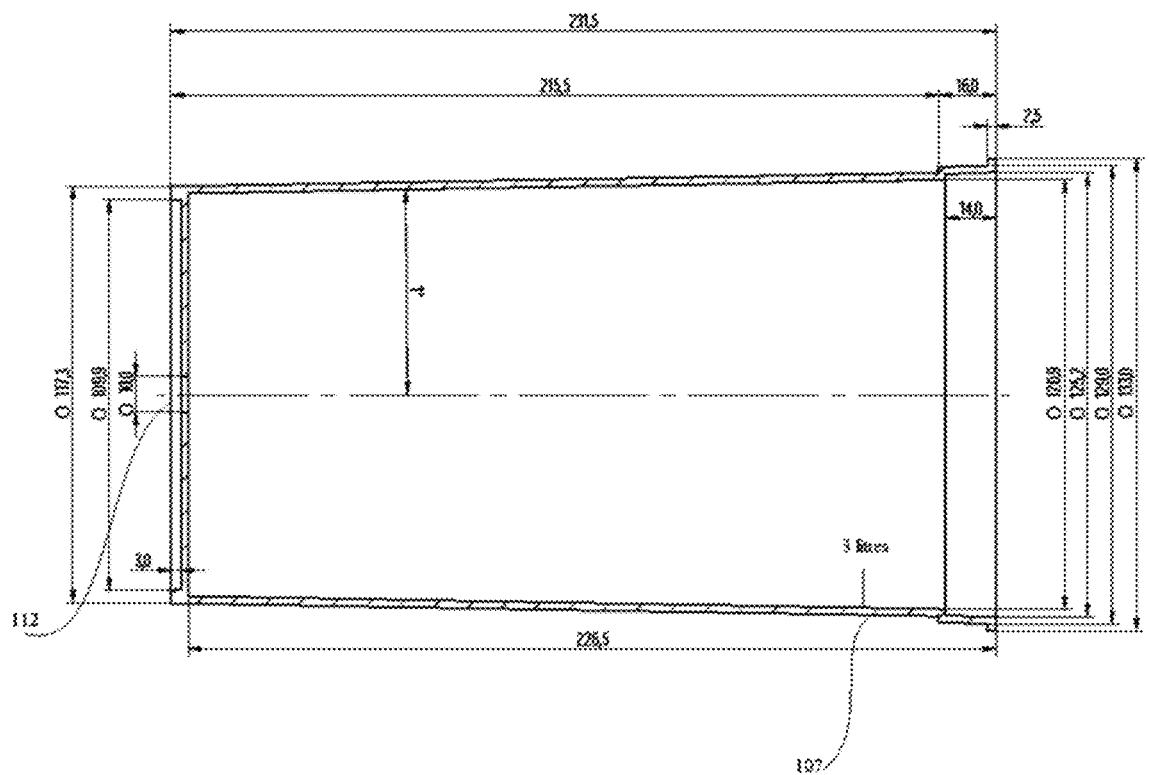
FIG. 4 illustrates a side view of the container as another preferred embodiment of the current invention

FIG. 4 illustrates a side view of the container as another preferred embodiment of the current invention. The figure shows the detailed dimensions of the container. The figure further shows the site of the attachment where it lie in the center of the container and is approximately 10O.

Figure 5:
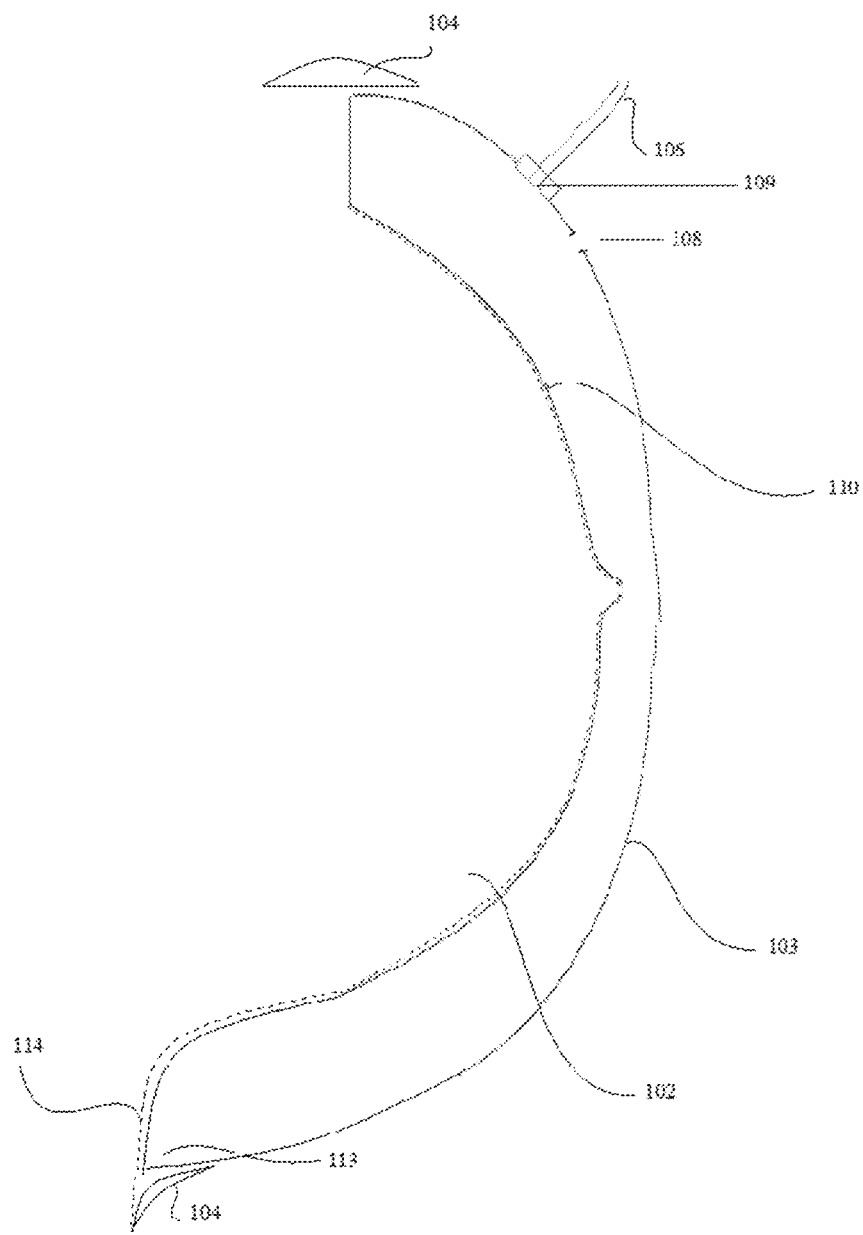
FIG. 5 illustrates a side close view of breast 102 of a female patient showing another embodiment of the current disclosure

FIG. 5 illustrates a side close view of breast 102 of a female patient showing another embodiment of the current disclosure are the peripheries of the cup shaped template 103 may to which a sealing element 104 fixedly attached. The sealing element 104 may be of any suitable material, such as rubber or plastic, and should be located tightly against the skin of the entire breast 102 of the patient. Preferable, the seal prevents communication between the space 105 formed inside the cup and with the exterior of the template, except through a tube connecting to the template 106. This will allow the tube 106 easily attached to a suitable container such as a graded cup 107 as shown in FIG. 1, which may contain a suitable fluid such as water. A quantity of water may thus pass into the space 105 to which it is connected. As fluid passes by gravity, air within the space will be displaced through the tube to the atmosphere. Once a drop of the fluid is out of the other opening 108 placed on the cup shaped template the water level read on the graded cup 107 is considered the measurement of breast volume.

In another embodiment of the current disclosure is a method of measuring breast volume to identify the desired size of the breast pre and post-operative, to measure the volume of the implant required to achieve the desired post-operative breast size, to verify that the post-operative breast size corresponds to the patient's desires and in another circumstances may be used as a follow up tool to monitor breast size.

As shown in FIGS. 1-5 another embodiment of the current disclosure; where the method includes one or more templates and each template has a cup portion appropriately embrace the entire breast 102. Said cup has an interior wall located in proximity to the breast 102 to be measured and a space 105 is formed between the breasts 102 and the cup of the template 103. The peripheries of the cup shaped template 103 may to which a sealing element 104 may be fixedly attached to avoid any leakage of fluid. The sealing element 104 may be of any suitable material, such as rubber or plastic, and should be located tightly against the skin of the entire breast 102 of the patient. Preferable, the seal prevents communication between the space 105 formed inside the cup and with the exterior of the template, except through a tube connecting to the template 106. This tube is attached to a suitable container such as a graded cup 107, which may contain a suitable fluid such as water. A quantity of water may thus pass into the space 105 to which it is connected. As fluid passes by gravity, air within the space will be expelled through the tube to the atmosphere. Once a drop of the fluid is out of the safety opening 108 placed on the cup shaped template the water level visible on the graded cup 107 is considered the measurement of breast volume.

It will be realized by those skilled in the art that it is not necessary to provide two templates to accomplish this task. Since each template is preformed, it could be utilized, first with one breast and then with the other as the cup shaped portion on is provided with four openings for the tube attachment and the other to expel of air, in which there are two on the right side and two on the left side as shown in FIG. 2.

As stated previously, those skilled in the art will quickly become aware of a wide variety of structures which could be employed to accomplish the method, within the scope of the disclosure both as to the apparatus and method.

The invention claimed is:

1. A device for measuring volume of a breast, the device comprising
a cup-shaped template of variable size to embrace a breast to be measured, the cup-shaped template comprising:
an interior wall located in proximity to the breast to be measured,
a first opening to permit passage of fluid into a space formed between the interior wall and the breast, and
a second opening to permit passage of air out of the space between said interior wall and the breast as the fluid is injected into said space; and
a sealing around periphery of the cup-shaped template for sealing contact between the cup-shaped template and skin of a patient with the breast to be measured,
wherein a skin contact surface of the cup-shaped template is non-flat, with a first lateral edge that contacts the skin extending further than an opposing second lateral edge that contacts the skin.

2. The device of claim 1, further comprising means for retaining said cup-shaped template against the skin of the patient so that said sealing is maintained in sealed relationship with the skin.

3. The device of claim 1, further comprising:
a container for providing the fluid and indicating a volume of the breast based on an amount of the fluid that is injected into the space through the first opening; and
a tube for transfer of the fluid from the container into the space via the first opening.

4. The device of claim 3, wherein the container is a graded container with measurement values indicative of an amount of the fluid injected into the space such that a measurement value corresponding to a level of the fluid in the container is directly indicative of the volume of the breast.

5. The device of claim 3, wherein the container and the tube are configured to inject the fluid into the space by gravity via the first opening located at a top side of the cup-shaped template.

6. A method of determining a volume of a human female breast, the method comprising:
inserting a breast to be measured into a cup-shaped template of predetermined volume;
sealing a periphery of the cup-shaped template to skin about the breast therein;
injecting a fluid from a graded container into a first opening the cup-shaped template about the breast therein;
stopping said injecting when air within the cup-shaped template has been expelled from a second opening of the cup-shaped template and fluid starts to overflow out of the second opening; and
determining a volume of the breast based on a fluid level visible on the graded container,
wherein a skin contact surface of the cup-shaped template is non-flat, with a first lateral edge that contacts the skin extending further than an opposing second lateral (medial chest wall) edge that contacts the skin.

7. The method of claim 6, further comprising performing the inserting, the sealing, the injecting, and the determining on another breast of a patient to determine asymmetry between the breast and the other breast.

8. The device of claim 1, wherein the cup-shaped template further comprises:
a third opening to permit passage of the fluid into the space formed between the interior wall and the breast; and
a fourth opening to permit passage of the air out of the space between said interior wall and the breast as the fluid is injected into said space, wherein the third opening and the fourth opening are provided on an opposing side of the cup-shaped template from the first opening and the second opening, and wherein the third opening and the fourth opening are closeable so as to be closed when the fluid is passed through the first opening, and the first opening and the second opening are closeable so as to be closed when the fluid is passed through the third opening, to permit contralateral breast measurements.

9. A device for measuring volume of a breast, the device comprising a cup-shaped template of variable size to embrace a breast to be measured, the cup-shaped template comprising:

an interior wall located in proximity to the breast to be measured, a first opening to permit passage of fluid into a space formed between the interior wall and the breast, a second opening to permit passage of air out of the space between said interior wall and the breast as the fluid is injected into said space, a third opening to permit passage of the fluid into the space formed between the interior wall and the breast, and a fourth opening to permit passage of the air out of the space between said interior wall and the breast as the fluid is injected into said space, a sealing around periphery of the cup-shaped template for sealing contact between the cup-shaped template and skin of a patient with the breast to be measured, wherein the third opening and the fourth opening are provided on an opposing side of the cup-shaped template from the first opening and the second opening.

10. The device as claimed in claim 9, wherein the third opening and the fourth opening are closeable so as to be closed when the fluid is passed through the first opening, and the first opening and the second opening are closeable so as to be closed when the fluid is passed through the third opening.

11. The device as claimed in claim 9, further comprising:

a container for providing the fluid and indicating a volume of the breast based on an amount of the fluid that is injected into the space through the first opening; and a tube for transfer of the fluid from the container into the space via the first opening.

12. The device as claimed in claim 11, wherein the container is a graded container with measurement values indicative of an amount of the fluid injected into the space such that a measurement value corresponding to a level of the fluid remaining in the container is directly indicative of the volume of the breast.

13. The device as claimed in claim 11, wherein the container and the tube are configured to inject the fluid into the space by gravity via the first opening located at a top side of the cup-shaped template.

\* \* \* \* \*